United States Patent
Buckman et al.

(10) Patent No.: US 7,322,995 B2
(45) Date of Patent: Jan. 29, 2008

(54) METHOD AND APPARATUS FOR VASCULAR AND VISCERAL CLIPPING

(75) Inventors: Robert F. Buckman, Radnor, PA (US); Jay A. Lenker, Laguna Beach, CA (US); Donald J. Kolehmainen, Laguna Niguel, CA (US)

(73) Assignee: Damage Control Surgical Technologies, Inc., Laguna Beach, CA (US)

( * ) Notice: Subject to any disclaimer, the term of this patent is extended or adjusted under 35 U.S.C. 154(b) by 633 days.

(21) Appl. No.: 10/663,038

(22) Filed: Sep. 15, 2003

(65) Prior Publication Data

US 2005/0251183 A1 Nov. 10, 2005

Related U.S. Application Data

(60) Provisional application No. 60/477,110, filed on Jun. 9, 2003, provisional application No. 60/410,635, filed on Sep. 13, 2002.

(51) Int. Cl.
*A61B 17/122* (2006.01)

(52) U.S. Cl. ......................... 606/157; 24/499
(58) Field of Classification Search ...................... None
See application file for complete search history.

(56) References Cited

U.S. PATENT DOCUMENTS

| | | | | |
|---|---|---|---|---|
| 2,250,605 A * | 7/1941 | Salem | .................. | 606/151 |
| 3,363,628 A * | 1/1968 | Wood | .................. | 606/158 |
| 3,509,882 A * | 5/1970 | Blake | .................. | 606/142 |
| 3,510,923 A * | 5/1970 | Blake | .................. | 606/158 |
| 3,802,437 A * | 4/1974 | Kees, Jr. | .................. | 606/142 |
| 3,805,792 A * | 4/1974 | Cogley | .................. | 606/142 |
| 3,911,926 A * | 10/1975 | Peters | .................. | 606/158 |
| 4,931,058 A * | 6/1990 | Cooper | .................. | 606/158 |
| 4,932,955 A * | 6/1990 | Merz et al. | .................. | 606/158 |
| 5,064,429 A * | 11/1991 | Waterman et al. | .................. | 606/151 |
| 5,099,827 A * | 3/1992 | Melzer et al. | .................. | 606/142 |
| 5,104,397 A * | 4/1992 | Vasconcelos et al. | .................. | 606/206 |
| 5,609,599 A | 3/1997 | Levin | .................. | 606/153 |
| 5,626,607 A * | 5/1997 | Malecki et al. | .................. | 606/205 |
| 5,674,231 A * | 10/1997 | Green et al. | .................. | 606/142 |
| 5,758,420 A * | 6/1998 | Schmidt et al. | .................. | 29/896.9 |
| 5,984,934 A * | 11/1999 | Ashby et al. | .................. | 606/151 |
| 6,641,575 B1 * | 11/2003 | Lonky | .................. | 604/540 |
| 6,802,848 B2 * | 10/2004 | Anderson et al. | .................. | 606/157 |
| 6,835,273 B1 * | 12/2004 | Vargas | .................. | 156/308.4 |
| 2005/0165429 A1* | 7/2005 | Douglas et al. | .................. | 606/157 |
| 2006/0190037 A1* | 8/2006 | Ginn et al. | .................. | 606/213 |

\* cited by examiner

*Primary Examiner*—Glenn K. Dawson

(57) ABSTRACT

Devices and methods for achieving hemostasis and leakage control in hollow body vessels such as the small and large intestines, arteries and veins as well as ducts leading to the gall bladder and other organs. The devices and methods disclosed herein are especially useful in the emergency, trauma surgery or military setting, and most especially during damage control procedures. In such cases, the patient may have received trauma to the abdomen, extremities, neck or thoracic region. The devices utilize removable or permanently implanted, broad, soft, parallel jaw clips with minimal projections to maintain vessel contents without damage to the tissue comprising the vessel. These clips are applied using either standard instruments or custom devices that are subsequently removed leaving the clips implanted, on a temporary or permanent basis, to provide for hemostasis or leakage prevention, or both. These clips overcome the limitations of clips and sutures that are currently used for the same purposes. The clips come in a variety of shapes and sizes. The clips may be placed and removed by open surgery or laparoscopic access.

12 Claims, 14 Drawing Sheets

METHOD AND APPARATUS FOR VASCULAR AND VISCERAL CLIPPING

This application claims priority benefit under 35 USC § 119(e) from U.S. Provisional Application No. 60/447,110 filed Jun. 9, 2003, and U.S. Provisional Application No. 60/410,635 filed Sep. 13, 2002.

FIELD OF THE INVENTION

The field of this invention is trauma surgery, combat medicine, and emergency medical services.

BACKGROUND OF THE INVENTION

As recently as the early 1990s, surgical operations for trauma were directed at the anatomic repair of all injuries at time of the initial operation. It was observed during these exercises that many patients became hypothermic, acidotic, and coagulopathic. Patients showing these three signs often died. Death often occurred in the operating room due to exsanguination, or postoperatively, due to the complications of prolonged shock and massive transfusion to replace blood lost as a result of the trauma.

One of the most notable developments in the recent evolution of surgery has been the reintroduction of the concept of staged laparotomy to overcome the deficiencies of the repair all-at-once approach. This new strategy of staged laparotomy employing new tactics that have been termed damage control is now used in 10% to 20% of all trauma laparotomies.

This strategy opens the way for a variety of new devices and methods for control of hemorrhage from solid organs or viscera. Although there are procedures for controlling these injuries, none of these procedures utilize optimal devices or tactics in their execution. Each area offers technological opportunities to improve the devices and procedures for applying those devices.

Two of the three immediate goals of damage control operations are to contain or stop, as quickly as possible, hemorrhage from major wounds of the solid viscera and to stop bleeding from injured intra-abdominal blood vessels. The third immediate goal of damage, control operations is to immediately arrest fecal or contents spillage from wounded hollow viscera. Such enteral wounds to the hollow viscera commonly occur in multiple areas of the bowel and colon. While existing methods and procedures, including the use of standard vascular instruments, bowel clamps, umbilical tape, and sutures, do allow the rapid control of vascular and visceral injuries in many cases, the standard techniques and tools have not been designed for temporary placement as part of a staged operation. Specifically, the vascular instruments or clamps have long handles that would be subjected to torque associated with temporary packing and closure of the abdomen. In addition, these instruments are not constructed of materials suitable for medium-term implantation and may have features that would cause the devices to become healed into the wound, rather than be easily removable.

During damage control procedures, time is of the essence. Every minute that passes without hemostatic control leads to further blood loss, shock and risk of intraoperative exsanguination. Every minute that passes without control of enteral spillage leads to increased risk of infection and septic death.

Typical vascular injuries requiring hemostatic control may include, for example, a wound to the descending abdominal aorta, the iliac arteries and veins, superior mesenteric vessels, vena cava or the portal vein, renal arteries and veins, and lumbar arteries. Typical enteric injuries requiring spillage control include wounds to the duodenum, small bowel, or colon. These wounds are, most commonly, multiple. The existing methods for controlling these include clamping and sewing, stapling, or resection of the involved bowel segment. All these current methods take much more time than the approach enabled by the methods and devices described below.

New devices, procedures and methods are needed to support the strategy of damage control in patients who have experienced abdominal injury. Such devices and procedures are particularly important in the emergency, military, and trauma care setting.

SUMMARY OF THE INVENTION

The devices and methods described below provide for improved treatment of wounds, including achieving hemostasis and leakage control in hollow body vessels such as the small and large intestines, arteries and veins as well as ducts leading to the gall bladder and other organs. The devices are clips for hollow vessels, variously designed to make them suitable for emergency closure of vessels. The clip is capable of partially occluding a structure with a tangential wound or completely obstructing both ends of a completely divided blood vessel or hollow viscus. It is highly desirable that clamps be designed to be left behind for a period of time ranging from several minutes to several days without the attached handles. The clamps are designed to minimize the chance of tissue ingrowth, thus allowing for improved ease of removal. The ideal clamp would have a very low profile, secure holding properties, be incapable of eroding into other structures, would not crush or destroy the wall of the clamped vessel, even if left for a period of days, would be easy to apply, would evenly distribute the compression force on the vessel, would be able to straddle, in a partially occluding way, a tangential wound of a major vessel or bowel. Features of the vascular and bowel clips include broad, controlled, force distribution on the tissue, even force distribution, both longitudinally and laterally on the vessel or bowel tissue. Additional key features of the vascular and bowel clips of the present invention include controlled movement, ease of placement, ease of locking in place, ease of removal, biocompatibility for medium to long-term implantation, minimal projections away from the clip, lack of sharp edges to cause further trauma during placement, and removal of the clip applier so that there are no long surfaces projecting from the clip area. The vascular and bowel clips may be placed through an open surgical access site or through a laparoscopic access and manipulation system.

Once a clip has been placed, it remains in place either temporarily or permanently. Temporary placement necessitates removal of the clip after a period of time. Long-term placement necessitates that the clip be able to sustain its function indefinitely. In this application, the clip is fabricated from materials that permit medium to long-term implantation. The clip design minimizes undercuts and features that would promote tissue ingrowth, thus restricting removal. In another embodiment, the clip may be fabricated, completely or partially, from resorbable materials that obviate the need to remove the clip in a subsequent surgical procedure. The clip applier is fabricated from materials that are suitable for short-term tissue or vascular contact. The clips themselves are fabricated from materials with smooth outer surfaces that do not encourage tissue or clot ingrowth. Thus, the clips may be removed with minimal re-bleeding.

The clips may be partially or entirely radiopaque so that they can be visualized on fluoroscopy or X-ray and easily located on subsequent follow-up.

The current medical practice of using sutures and current clips is not an optimized solution to open visceral and vascular wound repair. The current techniques almost always cause a tourniquet effect and require substantially more time to place than is desired, thus increasing the chance of accelerated deterioration of the patient's condition. The devices and methods described herein distinguish over the current medical practice because the present invention is tailored to the needs of open vascular or bowel repair. The clips have soft serrated jaws to grab the vessel wall and prevent spillage, but not strangulate the vasculature within the wall. They have short stubby grasping handles that are activated by tools that provide mechanical advantage and extension of reach into small spaces. The clips are suited for either open surgical implantation and removal, or they are suited for laparoscopic placement and removal using specialized access, grasping and delivery instruments. When the clips of the present invention are removed from the patient, re-bleeding does not occur because there is minimal penetration of the wound tissues or clot into the interstices of the clips.

Another feature of the clips is reduction in the length of those portions of the implantable clip (the actuating lever arms) that projects away from the actual clamping surface. This minimization of projection away from the clamping surface is accomplished by use of more than one hinge point, telescoping members and applier grasping points located between the hinge point and the clamping surface. In another embodiment, the grasping tabs projecting away from the clip are minimized by folding them in a direction opposite to that in which they are compressed to open the clip. Folding the tabs back onto the clip allows the tabs to be completely or nearly completely eliminated as a projection. The folding tabs have their own hinge points or they rotate around the main clamp axis. In another embodiment, the tabs are rotated perpendicular to the direction of compression to move them out of the way so that they do not project away from the clip jaws.

Another feature of the clips is the parallelism of the jaws. In the closed or nearly closed configuration, the jaws separate and close along a linear path rather than an arcuate path. Thus, there are no pinch points near the hinge area of the clips. The clips comprise hinges that permit linear or nearly linear travel. This linear travel feature near the closed position means that the jaws close with even, predictable force distribution on the vessel.

Another feature of the clips is the broad force distribution both longitudinally along the vessel to be clipped and laterally across the vessel being clipped. These clips of the present invention are not narrow but, instead, are broad. They typically comprise circular or elliptical pads that can encompass a substantial amount of vessel tissue.

DETAILED DESCRIPTION OF THE INVENTION

Figure 1A:
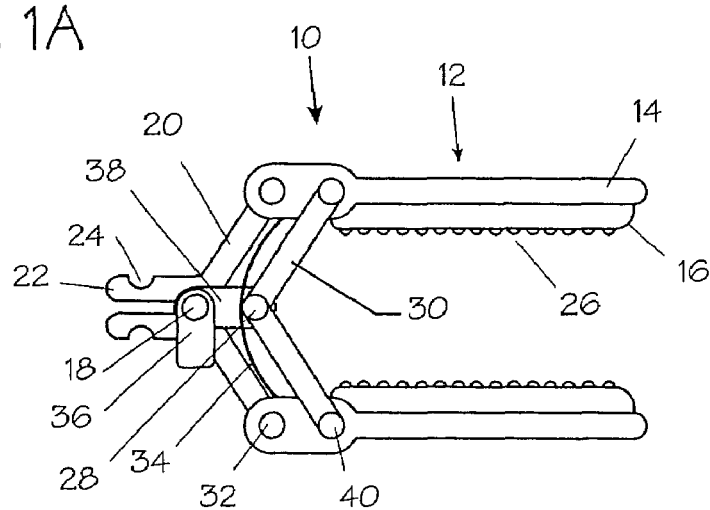
FIG. 1A illustrates a side view of the clip in its open state.

FIG. 1A illustrates a side view of a clip 10 of the present invention. The clip 10 comprises a plurality of jaws 12, further comprising a frame 14 and a pad 16, a main hinge 18, a plurality of main struts 20, a plurality of opening tabs 22, a plurality of grasping detents 24, and a plurality of optional serrations 26 on one or more of the pads 16. The clip 10 further comprises an optional secondary hinge 28, a plurality of optional secondary struts 30, a plurality of main pivot points 32, an optional spring 34, an optional lock 36, an optional hinge bracket 38, and a plurality of optional secondary pivot points 40.

Referring to FIG. 1A, the jaws 12 of the clip 10 are shown in their open configuration. The frame 14 provides rigid support and orientation for the pads.16. The top and bottom frames 14 are connected to a main hinge 18 through a plurality of main struts 20. Each of the main struts 20 is rigidly affixed to the opening tab 22 with the grasping detent 24 formed into the opening tab 22. In this embodiment, the main hinge 18 is connected to the secondary hinge 28 by a plurality of hinge brackets 38. The main struts 20 are rotationally connected to the main hinge 18 and the main pivot points 32. The secondary struts 30 are connected to the secondary hinge 28 and the secondary pivot points 40. The serrations 26 are formed on the surface of the pads 16. The spring 34 is affixed between the main pivot points 32 and causes both of the frames 14 to be forced toward each other.

Further, referring to FIG. 1A, the clip 10 utilizes a parallelogram hinge design to facilitate parallelism in the jaws 12 in the open, closed and partially open configurations.

The clip frame 14, the main struts 20 and secondary struts 30 as well as the main pivot points 32, secondary pivot points 40, the main hinge 18, the secondary hinge 28, the plurality of hinge brackets 38 and the opening tabs 22 are fabricated from generally rigid materials such as, but not limited to, stainless steel, cobalt-nickel alloys, nitinol, tantalum, titanium, polylactic acid, polyglycolic acid, platinum, polypropylene, polyethylene, polyimide and the like. Where resorbable materials such as polylactic acid and polyglycolic acid are used, the clips will disintegrate within the body over a period of time, thus obviating the need to remove the clip 10, and preventing or limiting ingrowth or overgrowth of body tissue over the clip components, thus facilitating removal. The pads 16 are fabricated from non-rigid, compliant materials such as open or closed cell foam, low durometer elastomers, resorbable compliant materials, and the like. The foams may be fabricated from a variety of polymers including but not limited to polyurethane, polyvinyl chloride and the like. The frame 12 or at least one other component of the clip 10 is preferably radiopaque and visible under fluoroscopy or X-Ray. All or most components of the clip 10 are fabricated from resorbable materials such as PLA or PGA so that the clip 10 eventually erodes or dissolves and goes away (preferably after healing is complete).

The opening tabs 22 are rigidly affixed to the main struts. Inward force applied to the opening tabs 22 causes a moment arm to rotate the main struts 20 around the main hinge 18 to the open position. The grasping detents 24 permit an instrument, such as forceps, Allis Clamp, Kocher Clamp, or the like, to grasp the opening tabs 22 in such a way that they do not slip off inadvertently.

The spring 34 is, preferably, a leaf spring and is fabricated from materials such as, but not limited to, stainless steel 316L, titanium, Elgiloy, nitinol and the like. The spring 34 is affixed between the two jaws and is pre-loaded to force the jaws toward the closed position. The spring 34 is designed to compress the pads 16 around the body vessel or lumen with enough force to close the lumen of the vessel but not enough force to close the vasculature within the body vessel wall. For example, a bowel can be closed with a distributed pressure of 20 mm Hg or less while a blood vessel would be closed with a pressure exceeding blood pressure. Typical diastolic blood pressures in a shock patient may be as low as 50 mm Hg so this would be the typical upper limit of the pressure generated by a clamp designed to compress a section of bowel. Thus, the bowel clamp spring system will provide pressures in the range of 2 to 50 mm Hg and more preferably between 10 and 20 mm Hg. The pressure may be calculated as the force applied by the spring 34 divided by the surface area of one of the pads 16. The spring characteristics, such as the spring material, size, thickness, etc. are selected to achieve the desired spring force and resultant clamping force applied by the clip. When used to close a blood vessel, the clamping force is preferably much higher. A vascular clamp system is required to seal off a blood vessel at a systolic blood pressure of 100 to 300 mm Hg in hypotensive and hypertensive patients, respectively. Accordingly, clamps intended for use on blood vessels are provided with springs of sufficient strength such that the clamps can apply a force of 100 to 300 mm Hg on the vessels to which they are applied. The pads 16 are soft and distribute the applied pressure evenly over the surface of the body vessel.

The pads 16 comprise optional serrations 26 that prevent slippage of the pads on the surface of the body vessel. The serrations 26 may be configured so as to impinge on each other tip to tip or they may be configured to interlock with each other. The pads 16 preferably comprise a central opening so that they provide a line of tissue compression, not a broad plane of compression. The supporting frame 14 is, also, preferably hollow and provides exposure to the tissue in its central region when looking in a direction perpendicular to the plane of the frame 14.

Figure 1B:
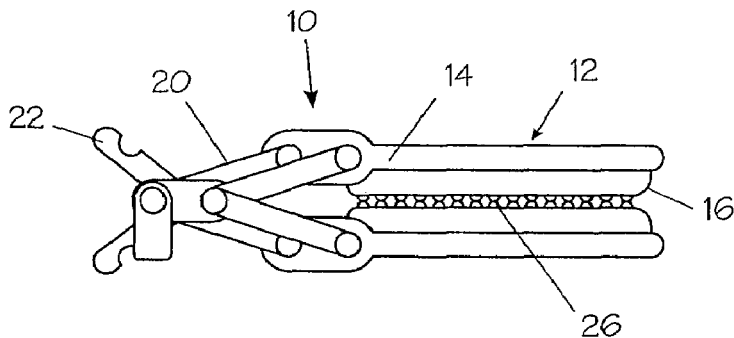
FIG. 1B illustrates a side view of the clip in the closed state.

FIG. 1B illustrates a side view of the clip 10 with the jaws 12 in their closed position. The opening tabs 22 are rotated apart and the serrations 26 on the pads 16 are in parallel touching contact. The maintenance of the parallel position of the jaws 12 permits closure of the vessel between the pads 16 without pinching and overcompression at one point and under-compression at another point. This feature of the clip 10 may be termed force parallelism and refers to an even force distribution on the tissue along the entire hinge-to-tip length of the clip.

The total projection of the non-jaw parts of the clip 10 with the jaws 12 in the closed position does not extend a distance greater than the distance D between the exterior of the closed frames 14 of the jaws 12. Thus, if the clip jaws 12 open to a maximum outside frame distance of 15 mm, the maximum total projection of any non-jaw 12 structure along a given axis when the jaws 12 are in the closed position will not be greater than 15 mm. Such non-jaw 12 projections include opening tabs 22, struts 20 and 30 and the like.

Figure 1C:
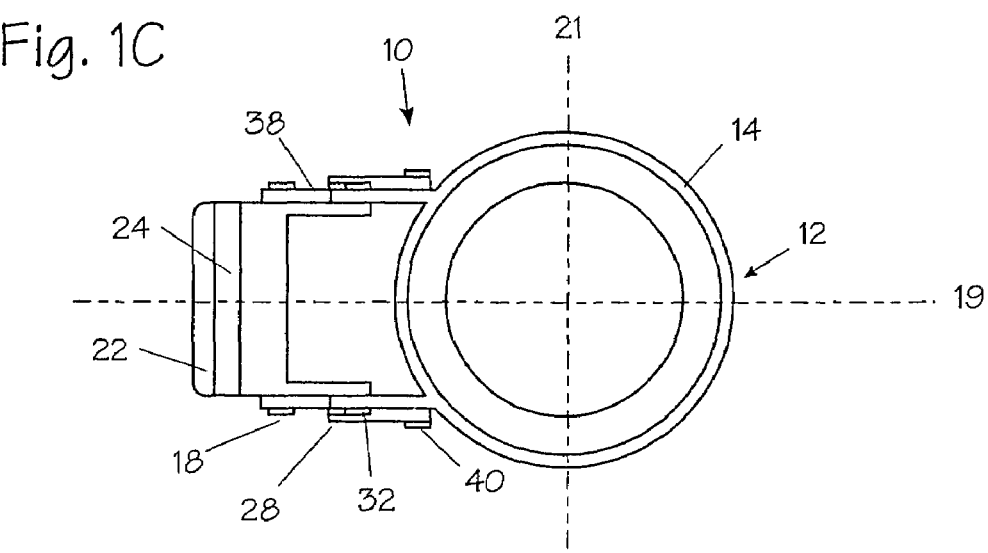
FIG. 1C illustrates a top view of a generally circular clip.

FIG. 1C illustrates a top view of the clip 10 comprising the jaws 12, further comprising the plurality of frames 14, the main pivot points 32, the secondary pivot points 40, the main hinge 18, the secondary hinge 28, the plurality of main struts 20 (not shown), the plurality of secondary struts 30 (not shown), the plurality of opening tabs 22, the spring 34 (not shown), and the plurality of grasping detents 24. The plurality of pads 16 are not visible in this view as they are on the other side of the frame 14.

Referring to FIG. 1C, the jaws 12, further comprising the frames 14 and the pads 16, are of a circular or donut configuration. In the preferred embodiment, the center of the frame 14 is open. In another embodiment, the center of the frame 14 could advantageously be closed. The jaws 12 project along a major axis (line 19), generally leading perpendicularly away from the main hinge 18. The jaws 12 project also along a minor axis (line 21) leading generally parallel to the direction of the main hinge 18. The jaws 12 are broad and are designed to encompass a large amount of tissue and, therefore have substantial major and minor axes. The minor axis (along line 21) of the jaw 12 should be no smaller than 25% of the major axis (along line 19) of the jaw 12 and, preferably no smaller than 40% of the distance subtended by the major axis. In another embodiment, the minor axis and major axis are switched, such that the major axis is parallel to the hinge and the longitudinal axis of the vessel to be closed.

Figure 2A:
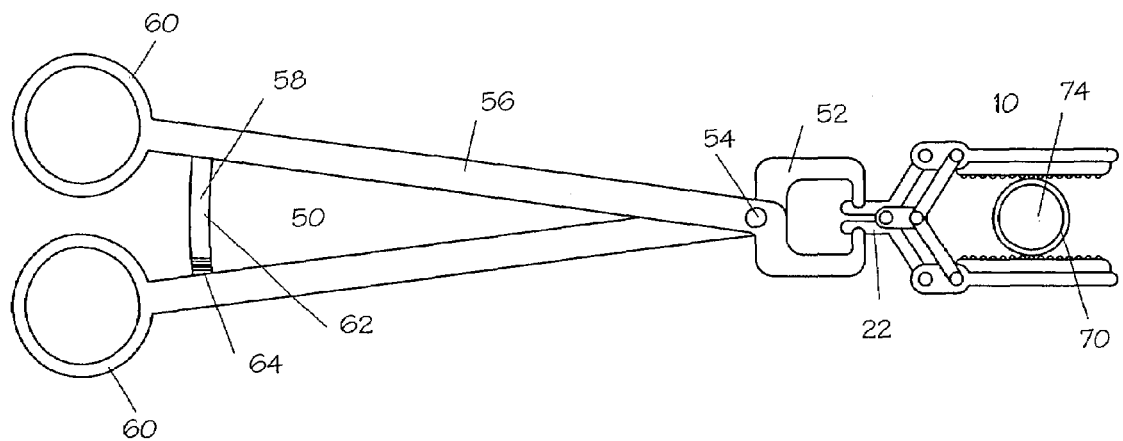
FIG. 2A illustrates a side view of the clip in the open position around a vessel with a clip applier attached.
Figure 2B:
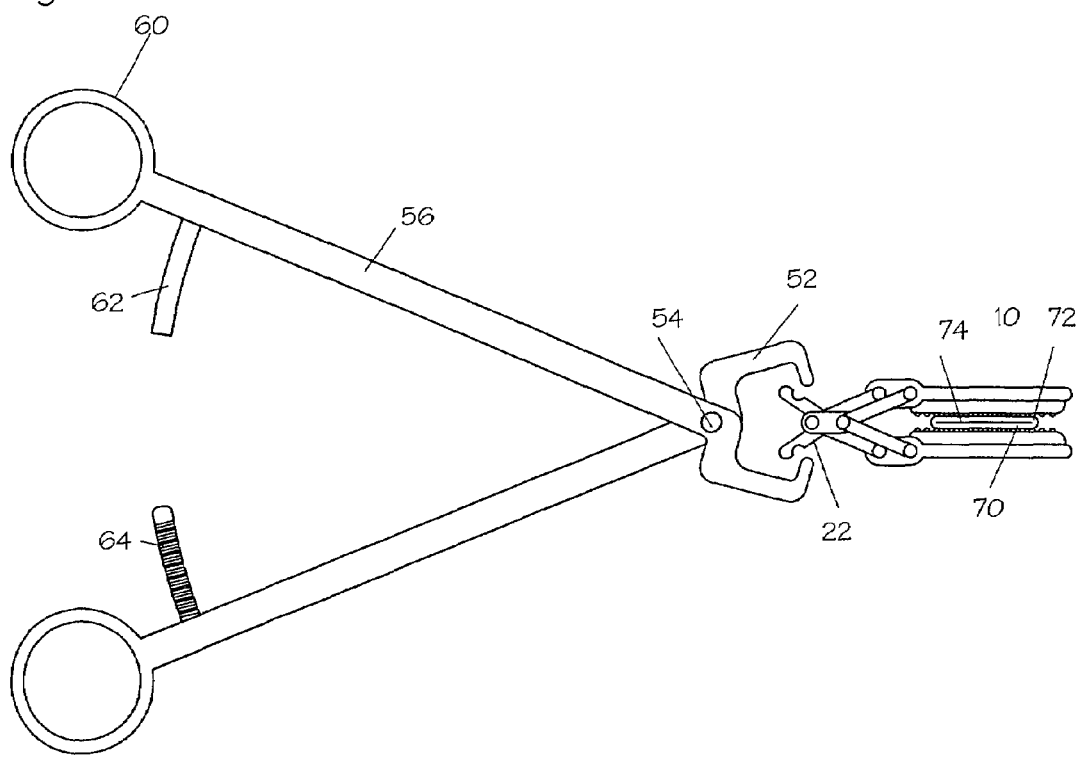
FIG. 2B illustrates a side view of the clip in the closed position occluding the vessel with the clip applier removed.

In FIG. 1C, the opening tabs 22 are aligned so that the main hinge 18 is located between the opening tabs 22 and the main struts 20. In yet another embodiment of the clip 10, the opening tabs 22 are positioned between the main hinge 18 and the frames 14. In this embodiment, the main struts 20 are forced open by force applied to the opening tabs 22. However, the projection of the opening tabs 22 beyond the main hinge 18 is eliminated, thus minimizing the projection of the clip 10 and minimizing its profile. Such minimized profile is advantageous when leaving the clip 10 implanted within the patient. Referring to FIGS. 2A and 2B, depending on the position of the opening tabs 22, the grasper jaws 52 on the graspers will be closed or overlapped closed to open the jaws 12 on the clip 10. The opening tabs 22 can also be positioned so that the grasper jaws 52 are open when the clip 10 jaws 12 are open. In a further embodiment, the grasper jaws 52 grab the main hinge 18 on the clip 10. A central shaft (not shown) is then advanced or retracted, pushing the opening tabs 22 to open jaws 12.

FIG. 2A illustrates a side view of a clip 10 of the present invention in the open position and aligned around a blood vessel 70. A grasping instrument 50 is positioned to open the clip 10. The grasping instrument 50 comprises a plurality of grasper jaws 52, a hinge 54, shafts 56, a ratchet lock 58 and finger loops 60.

Referring to FIGS. 2A and 1A, the grasper jaws 52 of the grasping instrument 50 are positioned within the grasping detents 24 on the opening tabs 22 of the clip 10. By applying inward pressure to close the two finger loops 60, the grasper jaws 52 are closed, thus closing the opening tabs 22 on the clip 10 and rotating the clip jaws 12 open against the force exerted by the spring 34. The ratchet lock 58 maintains closure of the grasper jaws 52, until such time as release is desired. The opened clip 10 is positioned around a blood vessel 70, further comprising a vessel wall 72 and a vessel lumen 74. In FIG. 2A, the vessel lumen 74 is open.

FIG. 2B illustrates a side view of the clip 10 of the present invention with its jaws 12 in the closed position and aligned around and occluding or closing the lumen 74 of the blood vessel 70. The ratchet lock 58 further comprises a ratchet lock top 62 and a ratchet lock bottom 64.

In this illustration, the ratchet lock top 62 on the grasper 50 has been separated from the grasper lock bottom 64, the finger loops have been rotated open and the grasper jaws 52 are open. The opening tabs 22 on the clip 10 are opened, allowing the spring (not shown) to bring the jaws 12 of the clip 10 into contact with and compress the vessel wall 72.

Referring to FIGS. 2A and 2B, such graspers 50 may be forceps or other commercially available instruments such as a Kocher Clamp, an Allis Clamp, or the like. In order to fully utilize the benefits of the invention, however, specialized graspers 50 may be desirable. This is especially true in the embodiment where the opening tabs 22 on the clip 10 are located between the main hinge 18 and the jaws 12. In this embodiment, a grasper jaw 52 that specifically mates with the internal opening tabs 22 and forces the opening tabs 22 open will be advantageous. The long shafts 56 are advantageous for all applications since they extend the reach of the surgeon into tight spaces not normally accessible with the fingers. In addition, the long shafts 56 help apply a large moment around hinge 54 to move the jaws 52 against substantial spring force.

Referring to FIGS. 1A, 1B, 1C, 2A and 2B, the diameter of the jaws 12 of the clip 10 ranges from about 0.1 cm to 10 cm depending on the tissue being compressed. More preferably, the diameter of the clip 10 ranges from about 0.2 cm to 5 cm.

Figure 3A:
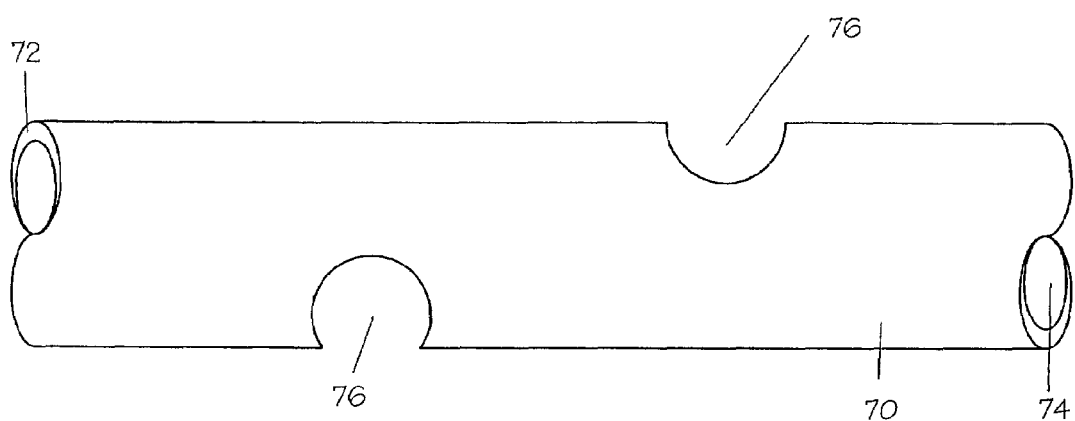
FIG. 3A illustrates a section of bowel with multiple transverse wounds.

FIG. 3A illustrates a longitudinal section of a bowel, blood vessel, or other body vessel 70. The bowel, blood vessel, or other body vessel comprises the wall 72 and the lumen 74. A plurality of wounds 76 further comprise this section of bowel, blood vessel, or other body vessel 70. These wounds 76 project into the lumen 74 but do not transect the entire vessel 70.

Figure 3B:
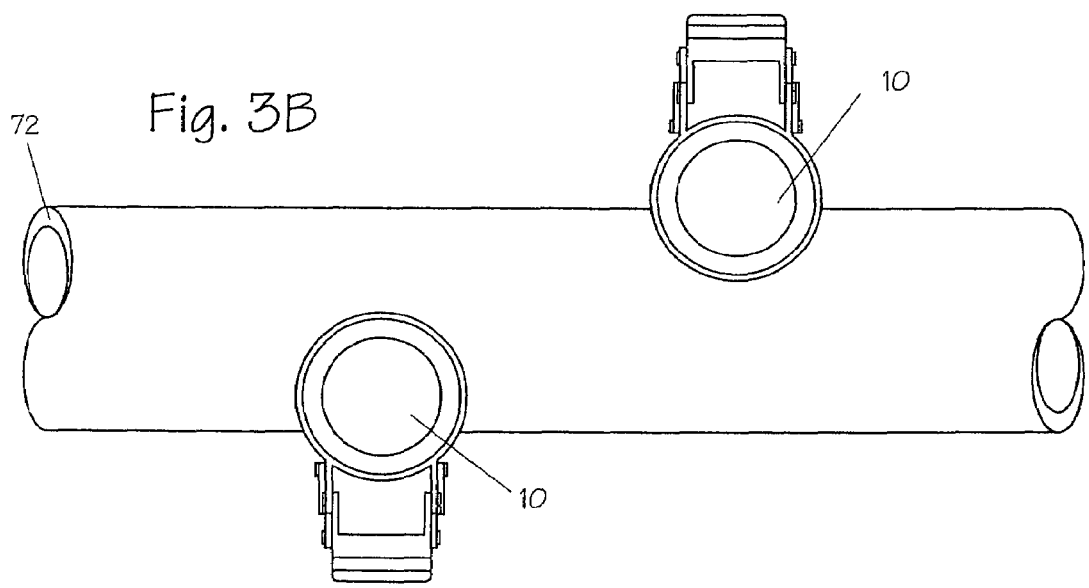
FIG. 3B illustrates the section of bowel with clips applied to prevent fecal spillage.

FIG. 3B illustrates the section of the bowel, blood vessel or other body vessel 70 with clips 10 applied over the wounds 76. The clips 10 are applied to the vessel wall 72 so as to completely seal off the lumen 74 from leakage. However, a through passage is still present within the lumen 74 of the vessel 70. For example, this configuration would permit perfusion of vasculature and tissue downstream of a blood vessel while stopping hemorrhage though the wounds 76.

Figure 4:
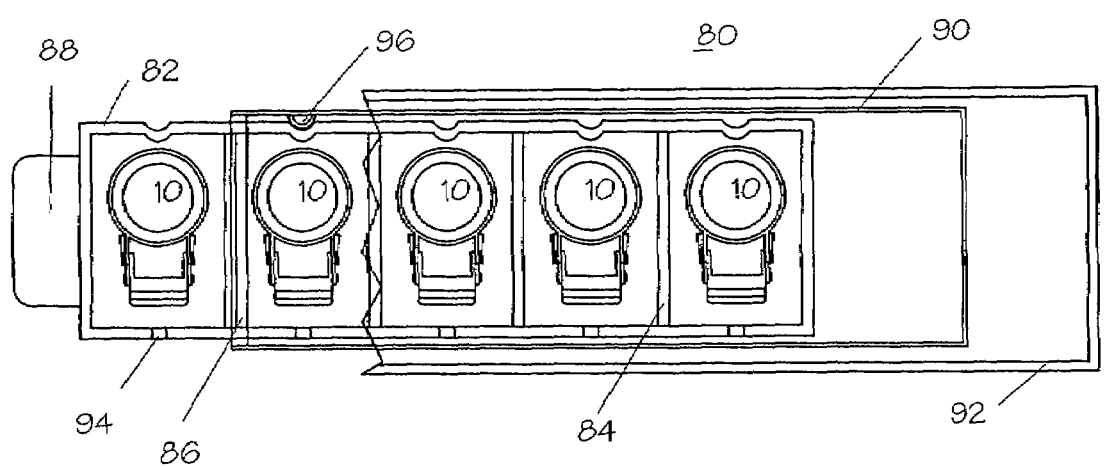
FIG. 4 illustrates a packaging system that delivers multiple clips in a convenient manner.

FIG. 4 illustrates a top view of a packaging system 80 for the clips 10. The packaging system comprises the plurality of clips 10, a carrier 82, a plurality of dividing walls 84, a sliding seal 86, a draw tab 88, a sterile barrier 90, an optional secondary sterile barrier 92, a plurality of guiding detents 94, and a plurality of notches 96.

Referring to FIG. 4, this embodiment shows five clips 10 located within the carrier 82 and separated by dividing walls 84. The optional secondary sterile barrier 92 is removed prior to accessing the sterile barrier 90 as part of double aseptic technique. The sterile barrier 90 is typically a polymer tray fabricated from thermoformed PVC, PETG, polystyrene, or the like. The secondary sterile barrier 92 is typically a heat sealed polyethylene or Tyvek® bag or polymer tray with a heat sealed Tyvek® lid, or the like. The carrier 82 further comprises a plurality of guiding detents 94 to facilitate positioning of the graspers 50 on the clips 10. The sliding seal 86 maintains sterility of each unused clip 10 while allowing access to one or more clip 10 at a time. The sliding seal 86 slides along the carrier 82 and seals against the dividing wall 84 to provide such sterile barrier. Optional notches 96 in the carrier and sterile barrier 90 provide tactile feel for locating the sliding seal 86 correctly on the dividing walls 84.

Figure 5A:
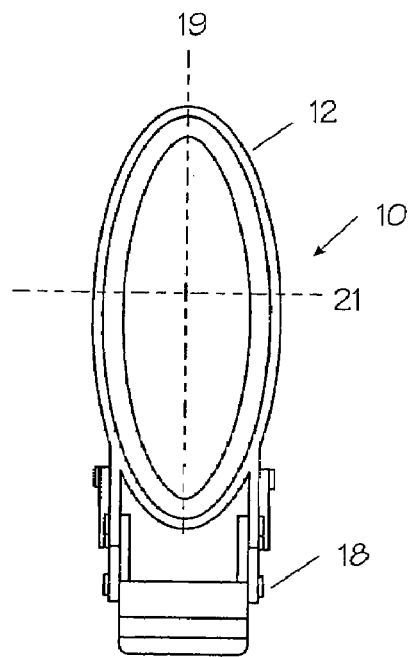
FIG. 5A illustrates a top view of an elliptical clip with its major axis oriented perpendicular to the clip hinge.

FIG. 5A illustrates the clip 10 of the present invention with the elliptical jaw 12 configuration. In this embodiment, the ellipse is oriented with its major axis parallel to the axis of the main hinge 18. The jaws 12 of the present invention project substantially in a direction lateral to the major axis of the jaws 12, which is generally perpendicular to the axis of the main hinge 18. The major axis of the jaws 12 can be defined as the axis moving away from the main hinge 18 or other moving part of the clip 10.

Figure 5B:
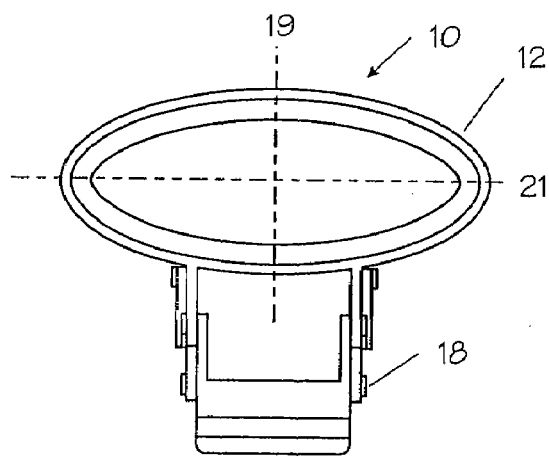
FIG. 5B illustrates a top view of an elliptical clip oriented with its major axis parallel to the clip hinge.

FIG. 5B illustrates the clip 10 of the present invention with the elliptical jaw 12 configuration. In this embodiment, the ellipse is oriented with its major axis perpendicular to the axis of the main hinge 18.

Figure 5C:
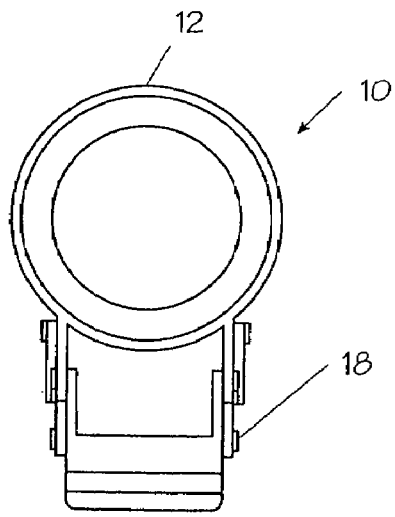
FIG. 5C illustrates a top view of a circular clip.

FIG. 5C illustrates the clip 10 of the present invention wherein the jaws 12 are of circular configuration.

Figure 5D:
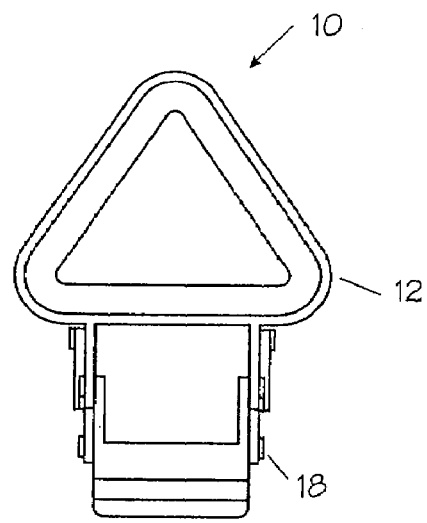
FIG. 5D illustrates a top view of a clip of with a rounded triangular configuration.

FIG. 5D illustrates the clip 10 of the present invention wherein the jaws 12 are of a rounded triangular configuration. The pointed side of the triangle is on the side of the clip 10 away from the main hinge 18. In another embodiment, the pointed side of the triangle is on the same side as the main hinge 18. Other geometric configurations may also be appropriate for the jaws 12.

Figure 6A:
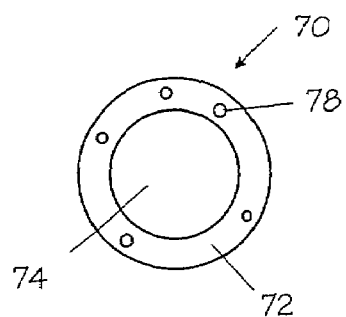
FIG. 6A illustrates a cross-sectional view of a bowel vessel wall showing the internal vasculature.

FIG. 6A illustrates an enteral vessel 70 in cross-sectional view. The enteral vessel 70 further comprises the wall 72, the lumen 74 and wall vasculature 78. The enteral vessel 70 is typically a bowel such as the esophagus, small intestine or large intestine but may also include other body lumens that are highly vascularized. The vasculature 78 includes arteries, veins and capillaries.

Figure 6B:
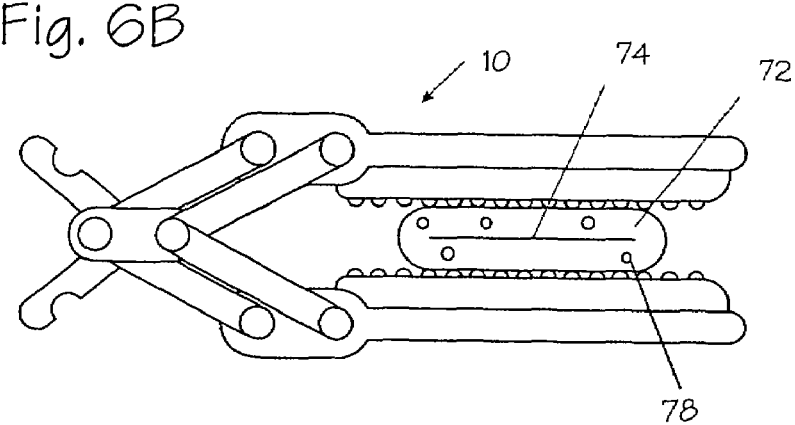
FIG. 6B illustrates a cross-sectional view of a bowel vessel wall with a clip applied preventing enteral spillage but maintaining blood flow within the internal vasculature.

FIG. 6B illustrates the enteral vessel 70 with the clip 10 applied to the exterior of the wall 72 so as to completely collapse and seal the lumen 74. The pressure exerted by the clip 10 is sufficient to close the lumen 74 but not enough to cause collapse of the vasculature 78.

Figure 6C:
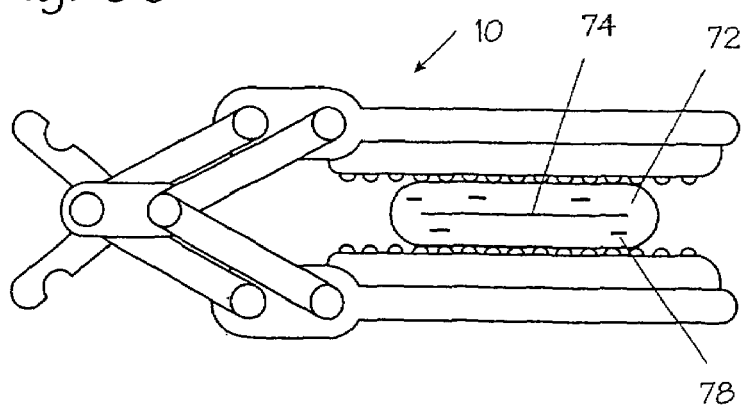
FIG. 6C illustrates a cross-sectional view of a bowel vessel with a clip applied preventing enteral spillage but also causing collapse of the vasculature internal to the bowel vessel wall.

FIG. 6C illustrates the enteral vessel 70 with the clip 10 applied to the exterior of the wall 72 so as to completely collapse and seal the lumen 74. The pressure exerted by the clip 10 is sufficient to not only close the lumen 74 but is also sufficient to cause collapse of the vasculature 78.

Figure 7A:
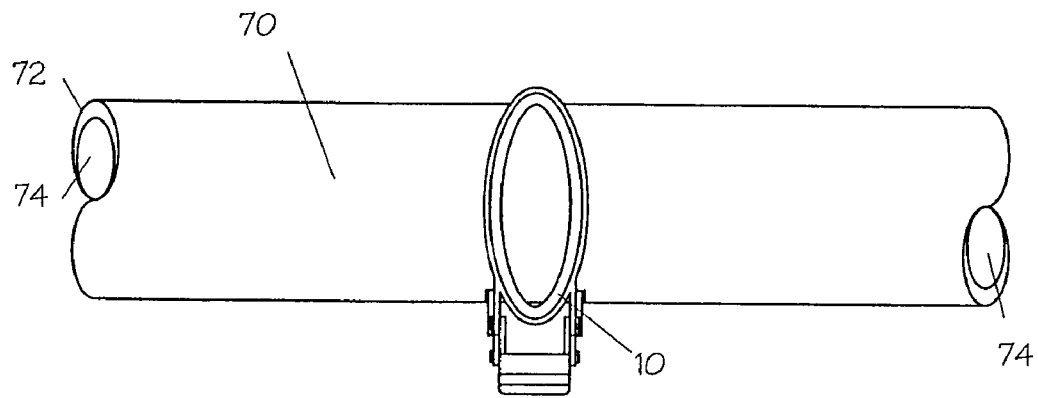
FIG. 7A illustrates a top view of a blood vessel that is completely occluded by a clip.

FIG. 7A illustrates a top view of a section of vessel 70 with a clip 10 applied so as to completely occlude the lumen 74 all the way across the width of the vessel 70.

Figure 7B:
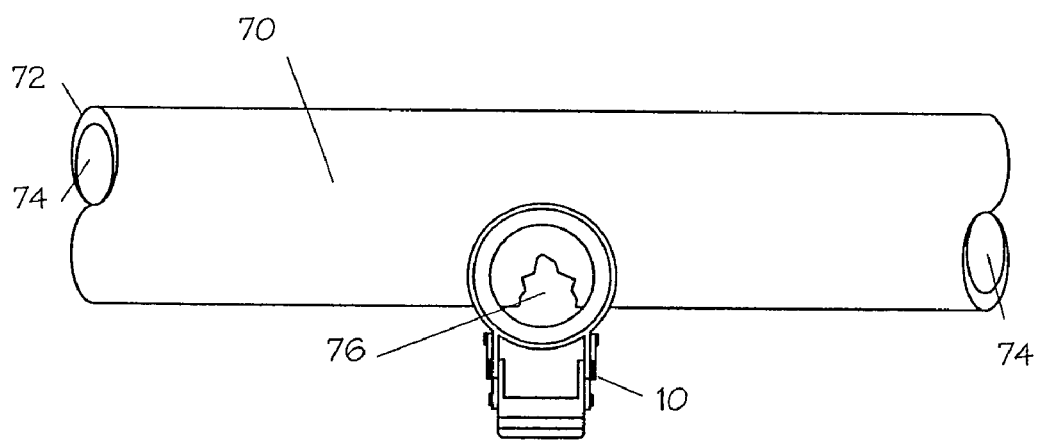
FIG. 7B illustrates a top view of a blood vessel that is partially occluded by a clip.

FIG. 7B illustrates a top view of a section of vessel 70 comprising the wound 76 partially severing the vessel wall 72. The clip 10 applied so as to completely occlude the lumen 74 around the wound 76 but still allowing some flow through lumen 74 in the region not collapsed by the clip 10. The large width of the clip 10 facilitates completely encircling and sealing the wound 76 to the vessel.

Figure 7C:
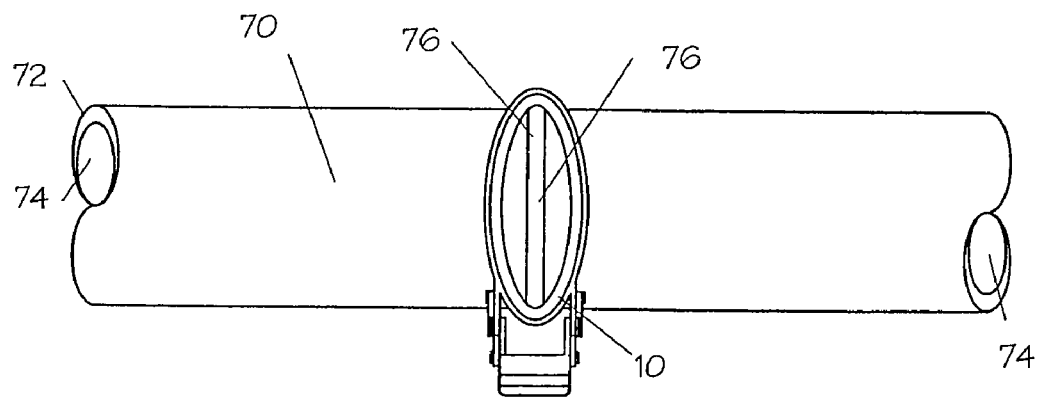
FIG. 7C illustrates a top view of a blood vessel that is completely severed and is completely occluded by a single clip.

FIG. 7C illustrates a top view of a section of vessel 70 comprising the wound 76 that completely transects the vessel wall 72. The clip 10 is applied to the vessel wall 72 of both of the severed ends of the vessel 70 so as to completely occlude the lumen 74 of both sections of the severed vessel 70. The large width of the clip 10 facilitates completely sealing the transecting wound 76 to both ends of the vessel.

Figure 8A:
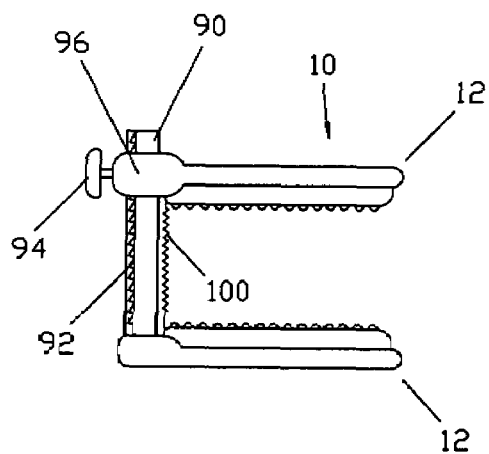
FIG. 8A illustrates a side view of a clip wherein the jaws move on linear axes and are open.

FIG. 8A illustrates another embodiment of a clip 10 of the present invention wherein one or more of the jaws 12 move along a linear bearing 90. In the preferred embodiment, the clip 10 comprises the jaws 12, the linear bearing 90, a plurality of linear ratchet teeth 92, a release 94, a ratchet lock 96, a spring 100, and an optional damper 102.

The clip 10 of the present embodiment is shown with the jaws 12 in the open position. One of the jaws 12 is permanently affixed to the base of the linear bearing 90. The other jaw 12 is permanently affixed to and moves with the ratchet lock 96 over the linear bearing 90. The plurality of linear ratchet teeth 92 are permanently affixed along the linear bearing 90 with the ramped ends toward the immovable jaw 12 and the flat ends away from the immovable jaw 12. The spring 100 is connected between the two jaws 12 so that the jaws are placed under the correct tension. The spring 100 pulls the jaws 12 together. The ratchet lock 96 engages the plurality of linear ratchet teeth 92 with a spring-loaded tooth and may be easily moved away from the immovable jaw 12. The ratchet lock 96 cannot move toward the immovable jaw 12 unless the release 94 is depressed. At this time, the spring 100 forces the jaws together. The optional damping system 102 (not shown) may be used to prevent too quick a movement of the movable jaw 12 toward the immovable jaw 12.

Referring to FIGS. 1A and 8A, the jaws 12 of this embodiment of the clip 10 are fabricated from the same materials and in the same configuration as the jaws 12 of the clip in FIG. 1A.

Figure 8B:
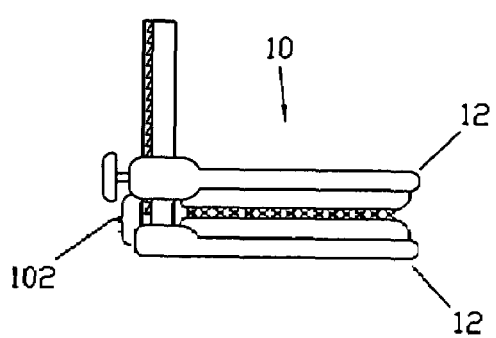
FIG. 8B illustrates a side view of the clip wherein the jaws move on linear axes and are closed.

FIG. 8B illustrates the clip 10 of FIG. 8A with the jaws 12 in the closed position.

Figure 8C:
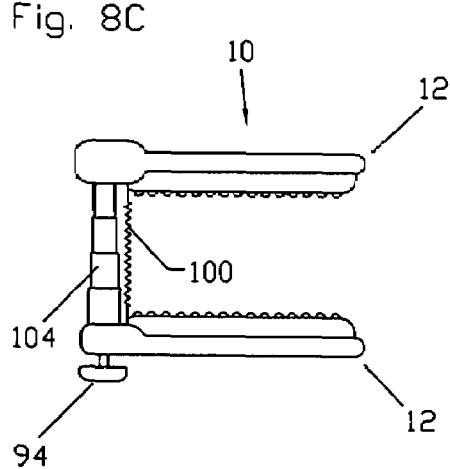
FIG. 8C illustrates a side view of the clip wherein the jaws move on linear telescoping axes and are open.

FIG. 8C illustrates another embodiment of the clip 10 of the present invention. The clip 10 comprises the jaws 12, a locking, telescoping linear bearing 104, a spring 100, an optional damper 102 (not shown) and a release 94.

The jaws 12 are held apart by the locking, telescoping linear bearing 104 against the compression force of the spring 100. The release 94 engages features within the telescoping, locking, linear bearing 104 to prevent compression until such time as the release 94 is depressed or otherwise activated. At this time, the spring 100 brings the jaws 12 together. The optional damper 102 controls the rate of jaw 12 movement.

Figure 8D:
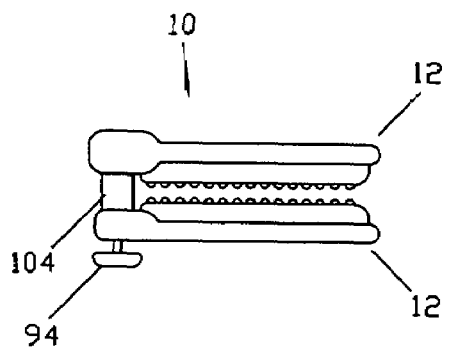
FIG. 8D illustrates a side view of the clip wherein the jaws move on linear telescoping axes and are closed.

FIG. 8D illustrates the clip 10 of the embodiment shown in FIG. 8C with the jaws 12 in the closed position. The telescoping, locking, linear bearing 104 is fully compressed and does not project beyond the perimeter of the clip 10 jaws 12. This embodiment minimizes the projections from the implantable clip 10, a particularly advantageous feature.

Figure 9A:
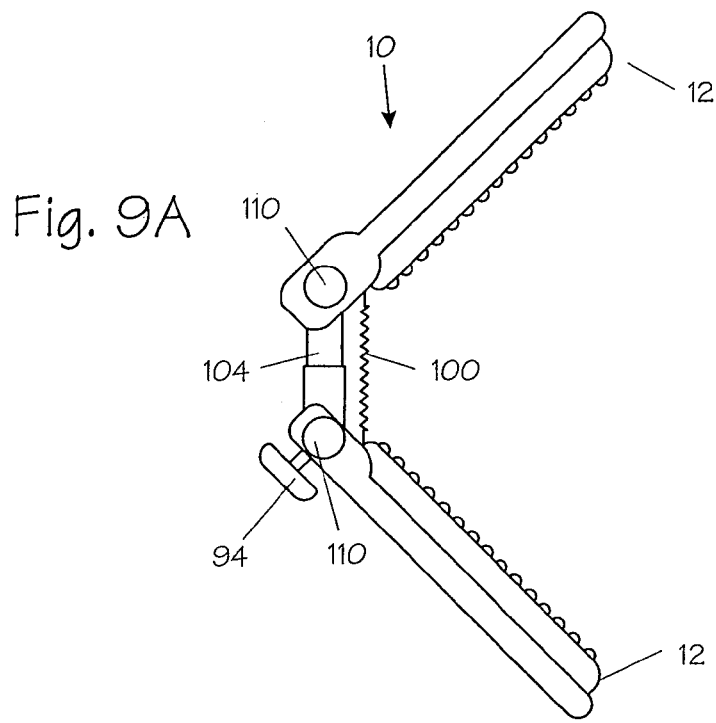
FIG. 9A illustrates a side view of a clip, shown with the jaws fully opened, wherein the jaws rotate angularly to encompass a wide vessel but close in a linear fashion on spring loaded telescoping linear bearings.

FIG. 9A illustrates another embodiment of the clip 10 of the present invention with its jaws 12 in the fully open position. The clip 10 comprises the jaws 12, a plurality of ratcheting hinges 110, a telescoping locking linear bearing 104, a release 94, a spring 100 and an optional damper 102 (not shown).

Referring to FIG. 9A, this embodiment of the clip 10 utilizes multiple opening mechanisms of rotation and linear separation. The plurality of ratcheting hinges 110 are affixed to the jaws 12. The telescoping locking linear bearing 104 is rotationally connected to the ratcheting hinges 110. The spring 100 is connected between the jaws 12 and acts to force the jaws 12 toward the closed position. The optional damper 102 (not shown) is affixed between the jaws 12 and controls the rate of jaw 12 closure.

The ratcheting hinges 110 are manually opened by rotation to allow for maximum separation of the jaws 12 so as to surround a large vessel.

Figure 9B:
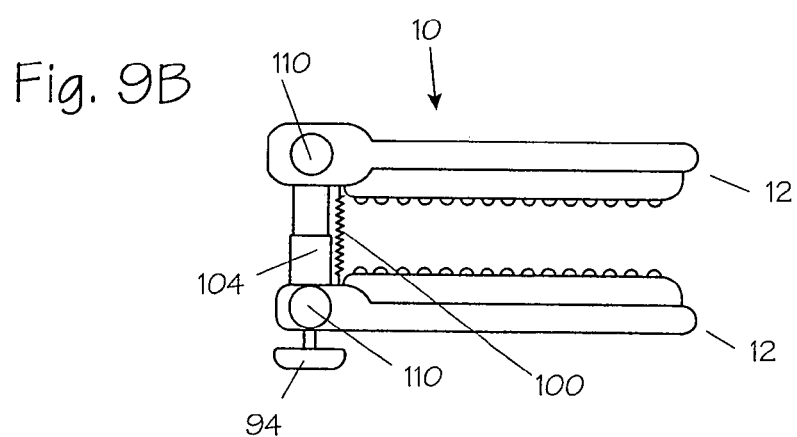
FIG. 9B illustrates a side view of the clip, shown with the jaws rotated to the parallel but slightly open configuration, wherein the jaws rotate angularly to encompass a wide vessel but close in a linear fashion on spring loaded telescoping linear bearings, shown with the jaws fully opened.

FIG. 9B illustrates the clip 10 of FIG. 9A with the jaws 12 in an intermediate position. The jaws 12 are closed manually on the ratcheting hinges 110. Following complete rotation, the jaws 12 are in the parallel position. The spring 100 is pre-loaded under tension in this configuration. The telescoping linear bearing 104 is in its fully open position.

Figure 9C:
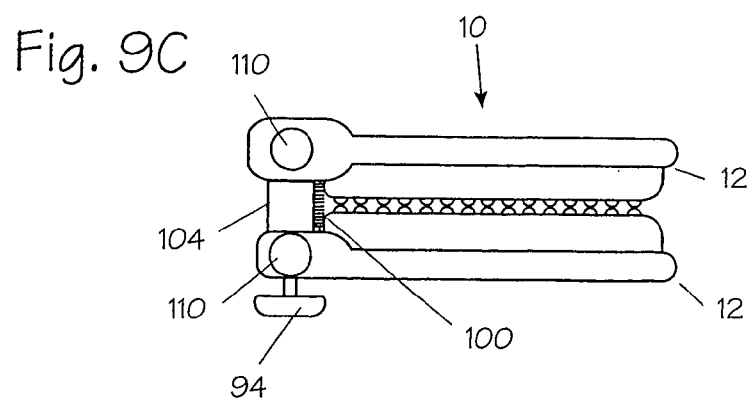
FIG. 9C illustrates a side view of the clip, shown with the jaws rotated to the parallel configuration and are fully closed, wherein the jaws rotate angularly to encompass a wide vessel but close in a linear fashion on spring loaded telescoping linear bearings.

FIG. 9C illustrates the clip 10 of FIG. 9A with the jaws 12 in the fully closed position. The spring 100 forces the jaws 12 closed after the release 94 is activated. The release 94 or a separate release (not shown) can optionally be used to unlock the jaws 12 for rotation about the ratcheting hinges 110. The telescoping linear bearing 104 is fully compressed in this configuration and does not project beyond the general envelope of the jaws 12. In practice, the spring 100 and the optional damper 102 are affixed inside the telescoping linear bearing 104.

Figure 10A:
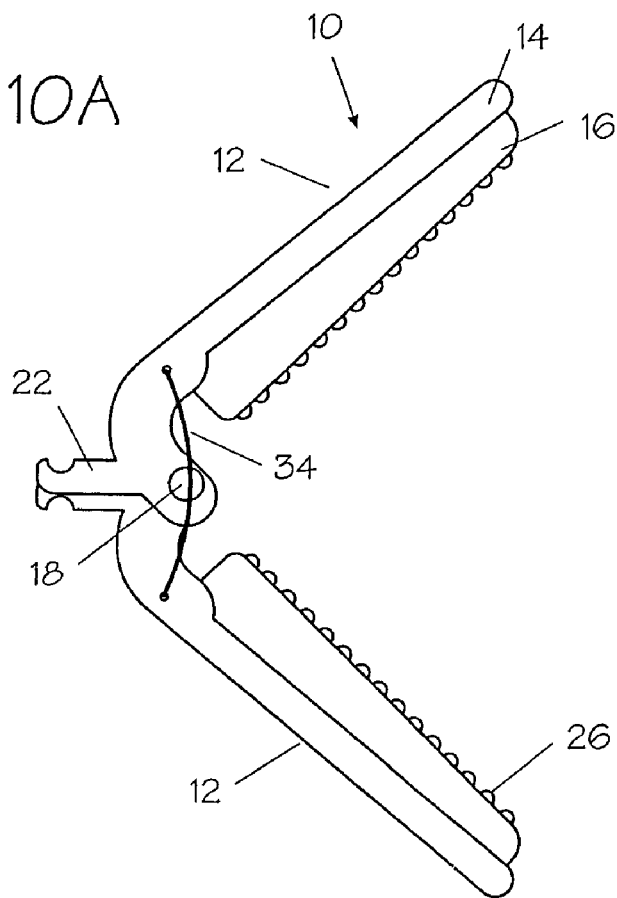
FIG. 10A illustrates a side view of the clip with the jaws rotated angularly to the open position wherein Pad material of variable thickness is used to equalize pressure distribution over the closed pads.

FIG. 10A illustrates yet another embodiment of the clip 10 of the present invention. The clip 10 is shown with the jaws 12 in the open position. The clip 10, in this embodiment, comprises a plurality of jaws 12 that are further comprised by a frame 14 and a pad 16. The jaws rotate around a main hinge 18. A plurality of opening tabs 22 are rigidly affixed to the frames 14. A spring 34 biases the jaws 12 toward the closed position.

Referring to FIG. 10A, by bringing the opening tabs 22 into close proximity, the jaws 12 are separated maximally. The pads 16 are designed with greater thickness toward the hinge 18. These variable thickness pads 16 help distribute the force on the tissue being clamped. The frames 14 are further apart toward the hinge than toward the outside of the jaws 12. This extra separation near the hinge helps prevent pinching the tissue and maximizes force distribution over the tissue. The pads 16 are fabricated from the same materials as those used in the clip 10 shown in FIG. 1A. In yet another embodiment of the clip 10 of FIG. 10A, the pads 16 may be of constant thickness but of decreasing hardness approaching the hinge 18. In this embodiment, the frames 14 of the jaws 12 could be roughly parallel to each other in the closed position.

Figure 10B:
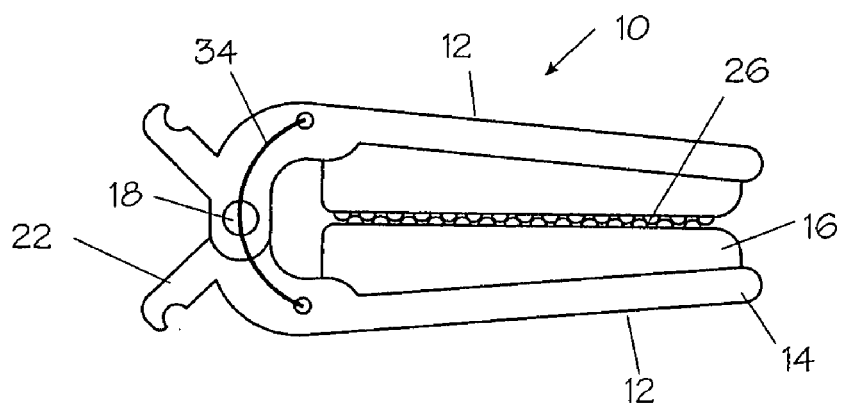
FIG. 10B illustrates a side view of the clip with the jaws rotated angularly to the closed position, wherein pad material of variable thickness is used to equalize pressure distribution over the closed pads.

FIG. 10B shows the clip 10 of FIG. 10A with its jaws 12 move to the closed position by the spring 34. Note that the interface between the pads 16 is even and parallel, even though the frame 14 of one jaw 12 is not parallel to the frame 14 of the opposing jaw 12. The opening tabs 22 are rotated apart around the hinge 18. While this embodiment of the clip 10 provides for approximately even (but not completely even) force distribution on the tissue with less complexity than the other clip 10 embodiments. The design relies on a very soft material in the construction of the pads 16. The serrations 26 are shown in an interlocking configuration.

Figure 11A:
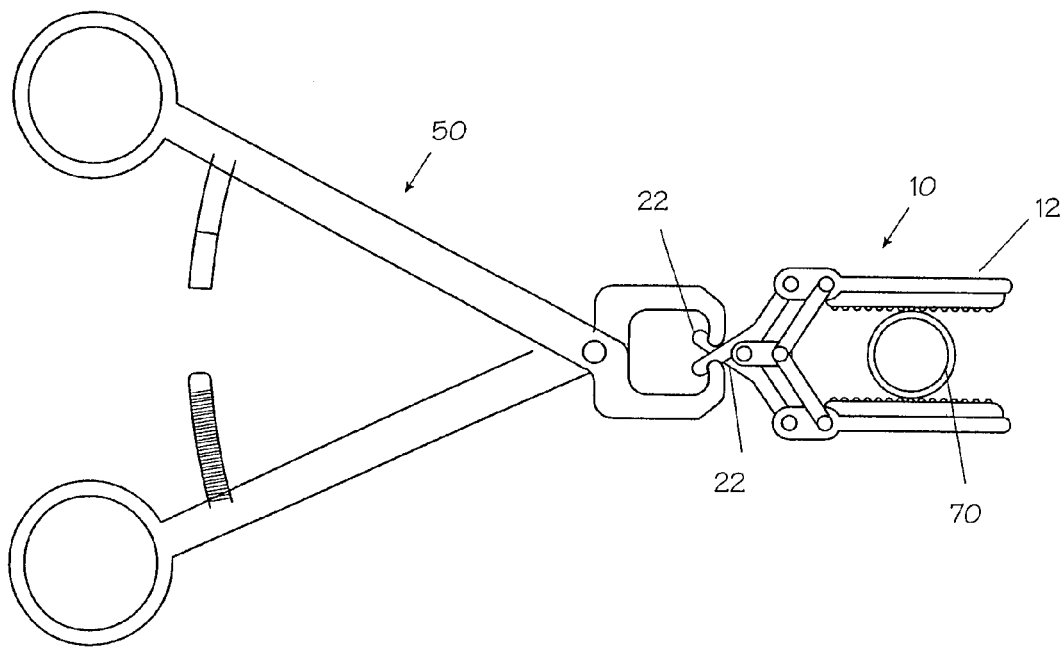
FIG. 11A illustrates a side view of the clip in the open position around a vessel with a clip applier attached, according to aspects of an embodiment of the invention. In this embodiment, the opening tabs are rotated outward with the clip in the open position.

FIG. 11A shows an open clip 10, comprising a plurality of opening tabs 22 and jaws 12, further comprising a plurality of frames 14 and pads 16, which are disposed around a vessel 70, and a clip applier 50, according to aspects of another embodiment of the invention optionally, a spring (not shown) is used to bias the jaws open or closed as required. In this embodiment, the opening tabs are angled apart when the clip jaws 12 are in the open position. The clip applier is open enough to grab the opening tabs 22.

Figure 11B:
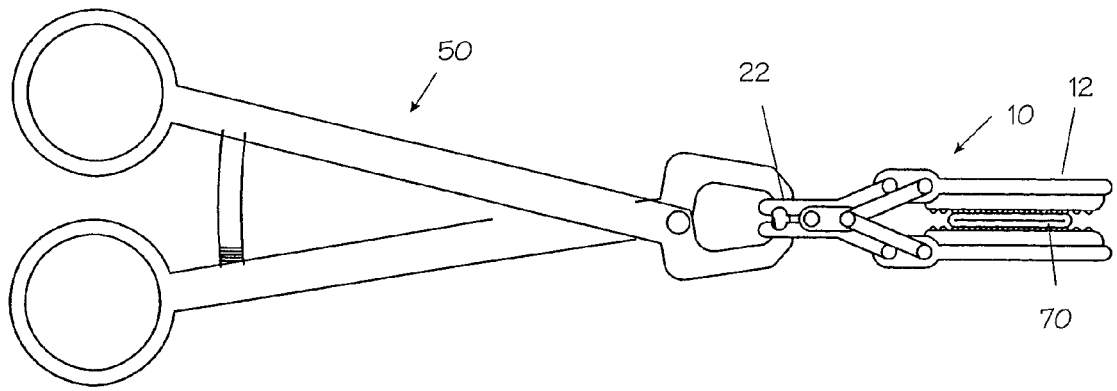
FIG. 11B illustrates a side view of the clip in the closed position occluding the vessel with the clip applier removed, according to aspects of an embodiment of the invention. In this embodiment the opening tabs are rotated inward to minimize projections with the clip in the closed position.

FIG. 11B shows a closed clip 10, comprising a plurality of opening tabs 22 and jaws 12, which are clamped to close the vessel 70. The clip applier 50 is closed sufficiently to force the opening tabs 22 closed, thus forcing the jaws 12 closed. The opening tabs 22 are now aligned parallel to the jaws 12 and have minimal or no projection out of the plane of the jaws, thus facilitating implantation. The clip applier 50 may also be configured to be closed when the jaws 12 of the clip 10 are open and open when the jaws 12 of the clip 10 are closed. This requires that the operator expand the clip applier 50 to close the jaws 12 of the clip 10, potentially an easier motion on the part of the operator. A ratcheting mechanism or locking mechanism (not shown) maintain the jaws 12 of the clip 10 in the closed position once positioned there by the clip applier 50.

Referring to FIGS. 2A, 3A, 3B, 4, 6A, 6B, 7A, 7B, 7C, and 11A, the methodology for implanting these clips 10, also known as clamps, is to place them through an open wound or incision. They are generally grasped by a grasping tool 50 and removed from their sterile package with the jaws 12 in the open position. The clips 10 are located properly over the vessel 70 or wound 76. At this point, the grasping tool 50 is opened and the jaws 12 of the clip 10 are allowed to close. Readjustment may be required in order to obtain the desired hemostasis or leakage control. The clips 10 are left implanted and the wound is covered appropriately until such time as the patient is stabilized and the wound can be correctly and permanently repaired.

Figure 12A:
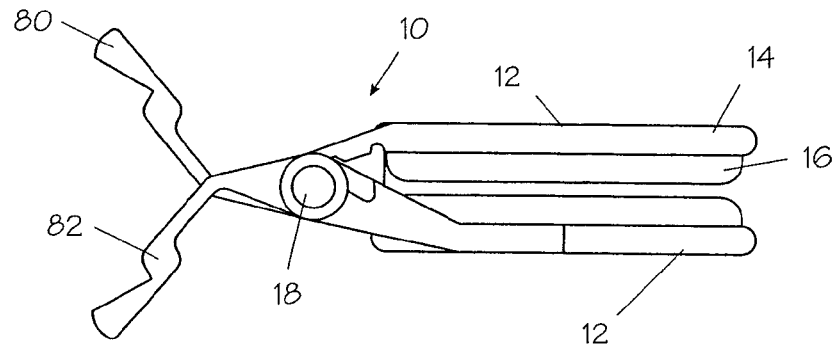
FIG. 12A illustrates a side view of the clip in the closed position with folding tabs unfolded and ready for compression.

FIG. 12A illustrates another embodiment of the clip 10 comprising a plurality of opposing jaws 12, further comprising a frame 14 and a pad 16, a hinge mechanism 18, an upper folding tab 80, a lower folding tab 82, and a spring, (not shown).

The jaws 12 rotate around the hinge mechanism 18 and are constrained radially by the hinge mechanism 18. The jaws 12 are fabricated using the frame 14 and the pad 16 which are permanently affixed to each other. The spring is affixed to the jaws 12 and is biased to force the jaws 12 together into the closed position. The upper folding tab 80 is radially constrained around the hinge mechanism 18 and is free to fold inward until it is essentially flush with the frame 14. The upper folding tab 18 has a projection that engages with the jaw 12 in the region of the hinge mechanism 18 so that when the upper folding tab 80 is forced downward by manual pressure, the upper jaw 12 is forced to rotationally open around the hinge mechanism 18. The lower folding tab 82 is radially constrained by the hinge mechanism 18 and rotates freely around the hinge mechanism 18 between pre-set limits. The lower folding tab 82, when forced upward, engages with a projection on the jaw 12 in the region of the hinge mechanism 18 and causes the lower jaw 12 to open.

Figure 12B:
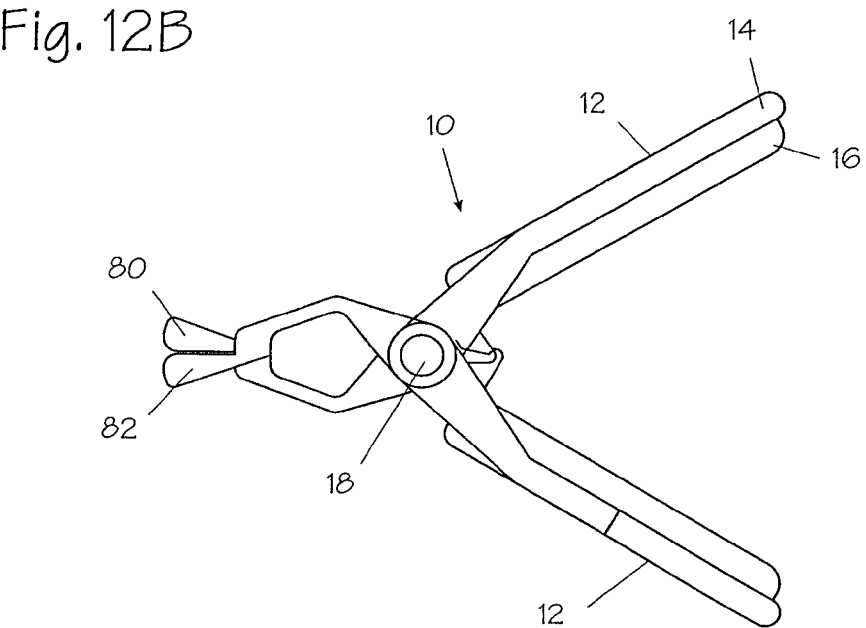
FIG. 12B illustrates a side view of the clip in the open position with the folding tabs compressed together and the jaws spread apart

FIG. 12B illustrates the clip 10 of the embodiment shown in FIG. 12A, with the jaws 12 in their open configuration. The upper folding tab 80 and the lower folding tab 82 have been compressed together forcing the jaws 12 to open.

Figure 12C:
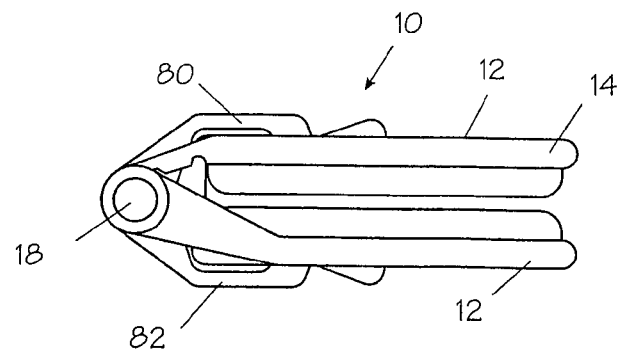
FIG. 12C illustrates a side view of the clip in the closed position with the jaws in opposition and the tabs folded inward to minimize projections.

FIG. 12C illustrates the clip 10 of the embodiment shown in FIG. 12A with the tabs 80 and 82 released and the jaws 12 closed by action of the spring (not shown). The upper tab 80 and the lower tab 82 have each been folded inward to be essentially flush with the respective frame 14 of the jaw 12. An optional locking detent or lock (not shown) is preferable to ensure that the folding tabs 80 and 82 remain in place once folded inward and until such time as release is desired. When release of the tabs 80 and 82 is desired, manual force is preferably used to overcome the lock and allow the tabs 80 and 82 to be folded outward so that they can be compressed to open the jaws 12.

The folding tabs 80 and 82 enable the clip 10 to be configured without any projections or with minimal projections so that they may be left in the body for a period of time, temporarily or permanently, and will not erode surrounding tissues.

In a further embodiment, the tabs 80 and 82 do not fold out but pull out from the clip 10 like a drawer. Once the tabs 80 and 82 have been used to open and then allow the clip 10 to close, the tabs 80 and 82 of this embodiment, are pushed inward so that they now comprise minimal or negligible projections. The tabs 80 and 82 slide on rails or slots in the clip 10, in this embodiment, and optionally comprise detents or interference locks to prevent unwanted outward expansion after the tabs 80 and 82 are pushed in.

Figure 13A:
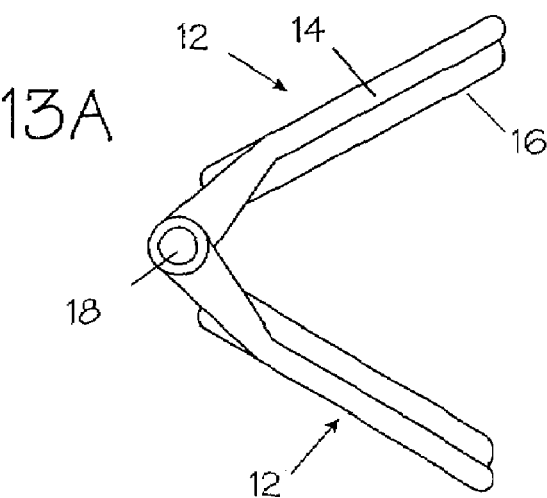
FIGS. 13A and 13B are side views of a clip with no tab projections beyond the hinge.
Figure 13B:
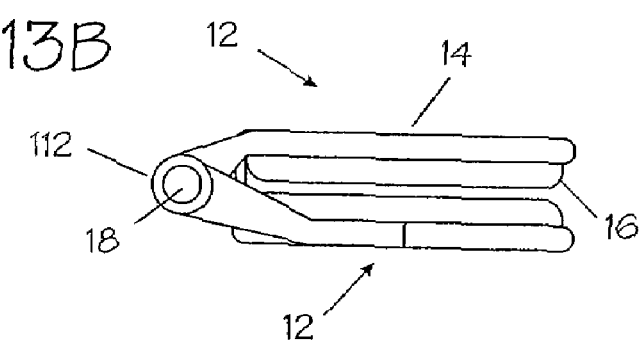
Figure 13C:
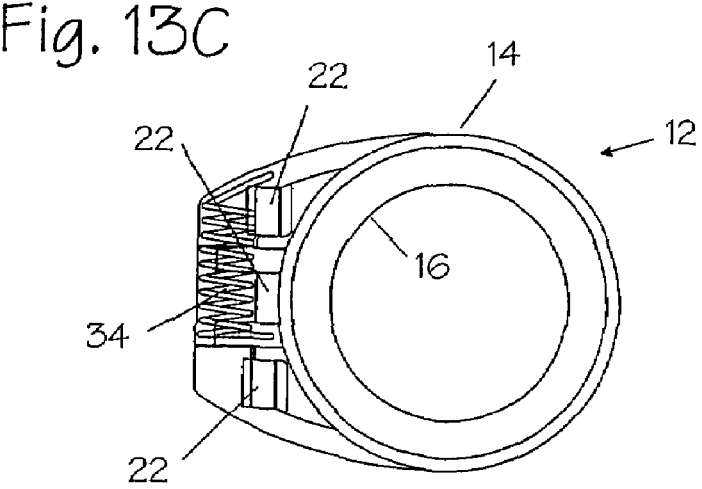
FIG. 13C is a top view of the clip of FIGS. 13A and 13A.

FIGS. 13A through 13C illustrate a clip 10 constructed without rearwardly extending opening tabs. FIGS. 13A and 13B are side views of a clip 10 with no tab projections beyond the hinge. The jaws are shown in the open configuration in FIG. 13A and in the close position in FIG. 13B. The jaws 12, frame 14 and a pad 16 are constructed as described above in relation to other embodiments of the clips. The hinge spring 18, which biases the clip to the closed position, is covered by a hinge housing 112. In this embodiment, the clamp jaws 12 are forced open by force applied to the opening tabs 22 with the specially adapted grasping instrument shown in FIGS. 14A and 14B. The opening tabs are positioned between the hinge 18 and the distal extent of the jaws. The projection of the opening tabs 22 beyond the main hinge 18 is thus eliminated, minimizing the projection of the clip 10 and minimizing its profile. This minimized profile is advantageous when leaving the clip 10 implanted within the patient. FIG. 13C is a top view of hinge shown in FIG. 13A. Though the spring is shown in this view, it will typically be covered by the hinge housing to provide a uniform rounded outer surface to the clip. The spring is concentrically wound around the hinge, having one end embedded in the lower jaw and one end embedded in the upper jaw. The spring biases the clip closed with a pre-determined, controlled force determined by the size and material of the spring. The spring characteristics are chosen to limit the force applied to the vessel, as described in relation to the leaf spring of FIGS. 1A through 1C. Grasping tabs 22 are visible between the hinge and the jaws. Preferably the tabs are arranged to avoid torsion on the clip, and the illustrated arrangement includes two spaced apart tabs attached one jaw, and a single tab on the opposite jaw, disposed under the gap established by the other tabs. The clip of this embodiment has rounded exterior surfaces and rounded edges.

Figure 14A:
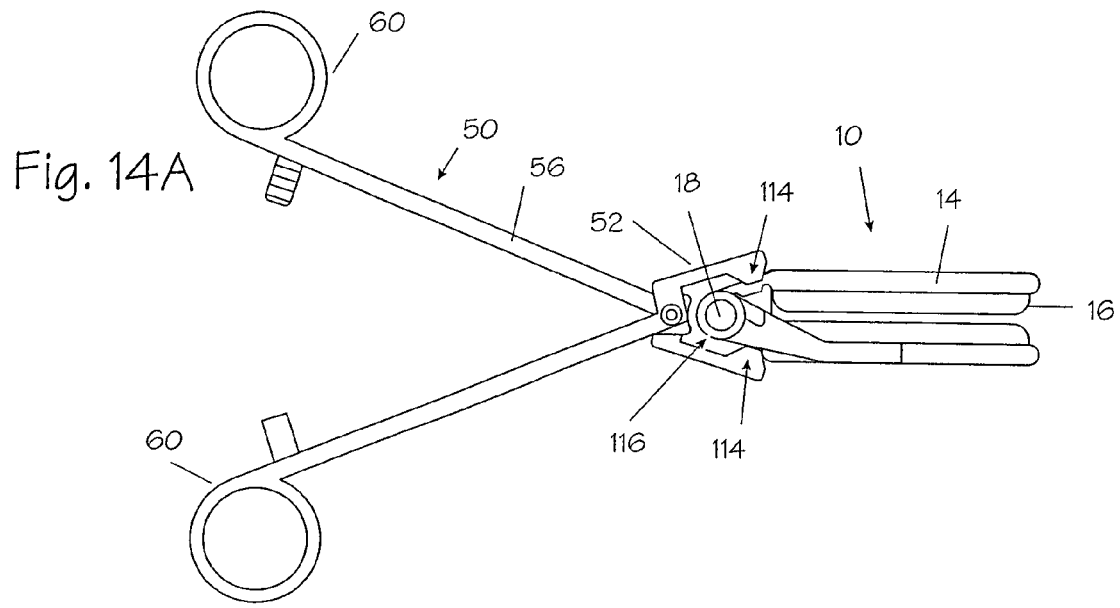
FIGS. 14A, 14B and 14C illustrate the clip applicator for use with the clip shown in FIGS. 13A through 13C.
Figure 14B:
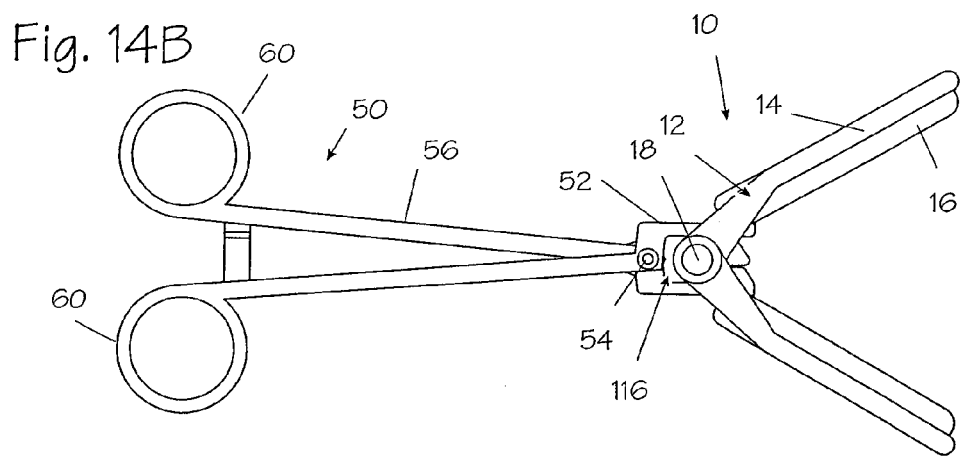
Figure 14C:
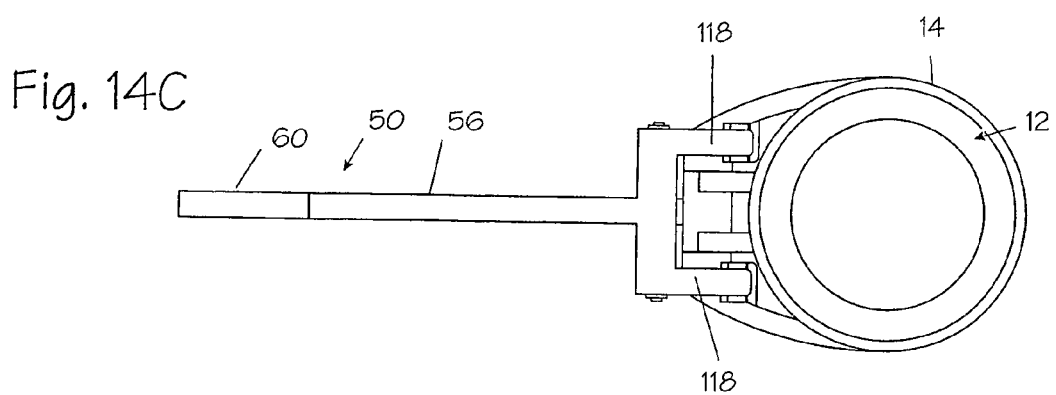

FIG. 14A the clip applier or grasping instrument 50 to be used with the clips of FIGS. 13A through 13C. The clip applier exerts force on tabs or surfaces between the hinge and the center of the jaws. The grasping instrument is constructed as described above, with the hinge 54, shafts 56, ratchet lock 58 and finger loops 60 described above. The grasper jaws 52 include bosses 114 which extend inwardly toward the opposite grasping jaw, leaving a hinge accommodating space 116 between the grasping jaw hinge 54 and the bosses. With the grasping instrument open, it can be positioned to place the clip hinge 18 into the hinge accommodating space, as shown in FIG. 14A, with the bosses in apposition to the tabs of the clip. As shown in FIG. 14B, when the grasping instrument is closed, the bosses force the tabs apart, thereby forcing the jaws open against the bias of the spring. FIG. 14C is a top view of the clip and clip applier of FIG. 14A and FIG. 14B. In this view, prongs 118 of one grasping jaw 52 are visible. The prongs of the clip applier project beyond the hinge of the clip so that they may exert force on pads or tabs located inward of the hinge.

Application of the implantable vessel clipping system provides improved speed of hollow organ, blood vessel and enteral trauma repair and minimizes the amount of hemorrhage and infection. The implantable nature of these clips facilitates damage control procedures wherein the patient can be allowed to stabilize prior to definitive repair of the injuries. Such damage control procedures have been shown to improve patient outcomes and save lives.

The present invention may be embodied in other specific forms without departing from its spirit or essential characteristics. For example, the spring-loaded clamps or clips can, instead, be closed on ratcheting mechanisms to a specific amount of compression, rather than by spring action. The spring-loaded clips may also be forced closed under the attraction force of opposite pole permanent or electronic magnets. Permanent magnets manufactured from neodymium iron boron are suitable for this purpose. The described embodiments are to be considered in all respects only as illustrative and not restrictive. The scope of the invention is therefore indicated by the appended claims rather than the foregoing description. All changes that come within the meaning and range of equivalency of the claims are to be embraced within their scope.

What is claimed is:

1. A surgical clip adapted for clipping of viscera comprising:
   a plurality of jaws,
   a plurality of grasping tabs,
   a hinge,
   a mechanism to keep the jaws closed,
   wherein said grasping tabs selectively fold inward against said jaws but may be folded outward to provide a grasping region to open said jaws.

2. The surgical clip of claim 1 wherein said jaws are ring-shaped and comprise an opening in the central region.

3. The surgical clip of claim 1 wherein the spring has spring characteristics which limit the force applied to the vessel to the range of 2 to 50 mm Hg.

4. The surgical clip of claim 1 wherein the jaws comprise a substantially oval shape.

5. A system for closing a wound in viscera having a lumen comprising:
   a surgical clip comprising a plurality of opposing jaws, wherein each jaw is rotatably disposed about a hinge, wherein the jaws comprise large, padded tissue contacting surfaces having a generally hollow open ring-shaped configuration, and further wherein the jaws substantially exert force parallelism when they contact a tissue;
   a spring operably engaging the jaws to bias the jaws shut;
   at least one opening tab secured to each jaw, wherein the opening tabs are disposed between the hinge and the distal extent of the jaw such that they do not extend proximally from the hinge; said opening tabs being operable to open and close the jaws; and
   a grasping instrument comprising a pair of jaws adapted to engage the opening tabs and apply force to the opening tabs to open the surgical clip, said jaws having a hinge accommodating space adapted to receive the hinge, and bosses located on the jaws so as to engage the opening tabs when the hinge is disposed within the hinge accommodating space;
   wherein the spring force of the spring is limited and pre-set so that the force applied by the clip to the viscera to prevent closure of blood vessels within the wall of the viscera while causing complete closure of the wall of the viscera being clipped against the loss of visceral contents.

6. The clip of claim 5 wherein said clip further comprises a plurality of serrations on the padded tissue contacting surfaces of the jaws.

7. The clip of claim 5 wherein said force parallelism is maintained by a parallelogram hinge.

8. The apparatus of claim 5 wherein said force parallelism is maintained by a linear bearing.

9. The apparatus of claim 5 wherein said force parallelism is created by a soft pad of non-uniform thickness.

10. The apparatus of claim 5 wherein said force parallelism is created by a soft pad of uniform hardness.

11. The apparatus of claim 5 further comprising a damper to regulate the speed of closure of the jaws.

12. The apparatus of claim 5 wherein said jaws comprise projections along a major and minor axis and where said jaws project along said minor axis at least 25% of the projection along said major axis of the jaw.

* * * * *